United States Patent [19]

Croll

[11] Patent Number: 5,425,635

[45] Date of Patent: Jun. 20, 1995

[54] MATRIX BAND SEGMENT AND RESTORATION PROCEDURE

[76] Inventor: Theodore P. Croll, 4242 Mechanicsville Rd., Mechanicsville, Pa. 18934

[21] Appl. No.: 260,805

[22] Filed: Jun. 16, 1994

[51] Int. Cl.6 .................................................. A61C 5/04
[52] U.S. Cl. ...................................... 433/39; 433/226
[58] Field of Search ..................... 433/39, 40, 155, 226

[56] References Cited

U.S. PATENT DOCUMENTS

| | | | |
|---|---|---|---|
| 424,790 | 4/1890 | Ivory | 433/39 |
| 677,268 | 6/1901 | Power | 433/40 |
| 1,669,231 | 5/1928 | Curran | 433/39 |
| 3,795,052 | 3/1974 | Mowery | 433/39 |

Primary Examiner—Cary E. O'Connor
Attorney, Agent, or Firm—Gregory J. Gore

[57] ABSTRACT

A matrix segment of sufficient size to cover the interproximal area of a tooth restoration is shaped for patient comfort, easy application, and easy removal. The smooth tapered shape of the segment sides provides adequate tooth coverage and minimizes potential gingival laceration. An aperture is located in the segment so that it may be conveniently pulled away after use with a string-like material, such as dental floss.

5 Claims, 1 Drawing Sheet

MATRIX BAND SEGMENT AND RESTORATION PROCEDURE

FIELD OF THE INVENTION

This invention relates to dentistry and particularly to the restoration of human teeth, using condensed silver amalgam or injected tooth colored restorative materials, and a means to enclose a bur cut preparation involving a proximal tooth surface.

BACKGROUND OF THE INVENTION AND DESCRIPTION OF PRIOR ART

Matrix bands are commonly used to confine the placement of a Class II dental restoration and to provide anatomical form to the restoration for proper proximal contact of posterior teeth. Matrix bands traditionally completely encircle the tooth and remain stable and inflexible during placement of the restorative material, providing the restoration with a smooth surface and assuring that properly condensed or injected restorative material will not escape the confines of the band, causing excess at cavosurface margins. A screw-tightened, mechanically-retained matrix band system, such as the Toffiemire retaining system is widely used. However, it has been shown that better anatomical proximal contour can be achieved with a custom-contoured, properly wedged, matrix band. The problem with custom-contoured wedged matrix bands is that they require a great deal of operating time. The use of individual matrix segments hand-cut from a long strip of suitable material which are then custom-shaped by the dentist during the restoration procedure is known, however, this process is also time-consuming and achieving intricate shapes of the matrix strips is not possible using dental hand cutting tools. There is, therefore, a need for a procedure using a matrix device that is easily formed, placed, and removed that provides the benefit of a custom-contoured wedge matrix band, but which saves operating time.

SUMMARY OF THE INVENTION

In order to fulfill the above-mentioned need in the art, the present pre-cut matrix band segment and procedure have been devised. The present invention employs a matrix segment which is custom-cut from a blank of metal suitable for matrix material to best carry out the novel procedure of the present invention. The segment is a portion of matrix material sufficient to cover the interproximal area of the restoration which is shaped for easy application and removal. According to the procedure disclosed herein, the matrix segment is properly shaped to the tooth contour, applied interproximally between the teeth, then wedged securely to the tooth. After the restorative material is placed and hardened initially, the wooden wedging is removed. The segment is then removed directly, lingually or buccally, preferably without displacement in the occlusal direction. Occlusal matrix removal can fracture setting amalgam. Application and removal of the segment is accomplished by use of pliers; or optionally, the segment may be removed by means of attaching and pulling it away with a string-like material such as dental floss or thicker dental tape.

More specifically, the applicant has devised a pre-cut matrix segment for dental restoration, comprising a planar segment of sheet metal having top and bottom portions with left and right sides, said top portion being wider than said bottom portion and said sides having smooth tapered edges converging in the direction of the bottom portion; said top portion including two laterally projecting ears, one on each side; and at least one of said ears including an aperture therein for receiving a string-like implement. The smooth tapered shape of the segment provides adequate tooth coverage and minimizes potential for gingival laceration which in turn provides for patient comfort. The contour of the metal segment also makes the device applicable to Class III or Class IV restorations of anterior teeth, either in its present form, or befit in half, upon itself, and inserted into proximal dental contact regions.

It is therefore the main object of the present invention to provide a molding device and procedure for achieving dental restorations of the Class II, Class III or Class IV type which is easily formed, placed and removed, thus saving operating time. Other objects, advantages and novel features of the invention will become apparent from the following detailed description of the invention when considered in conjunction with the accompanying drawings.

DESCRIPTION OF THE PREFERRED EMBODIMENT

Figure 1:
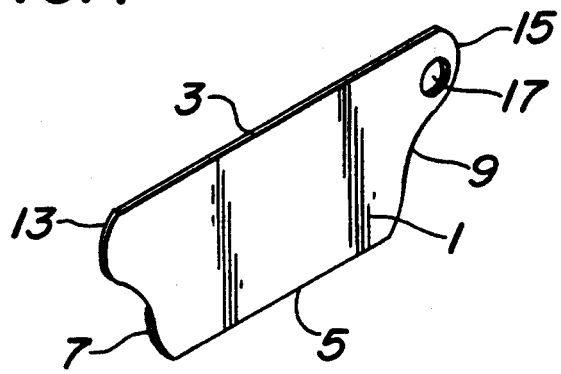
FIG. 1 is a top left front isometric view of the matrix band segment of the present invention.

Referring now to FIG. 1, the matrix band segment 1 of the present invention is die-cut from a sheet of ¼-hard surgical stainless steel sheet material. The segments of the present invention are produced in two optional thicknesses, 0.0015-inches and 0.0020-inches. This material is easily contoured with pliers and is suitable for primary molar and permanent Class II restorations. The segment has a top 3 and a bottom 5 portion with opposing left 7 and right 9 sides. The top portion is wider than the bottom portion, and to prevent laceration of the gingival tissues, the sides have smooth tapered edges. The sides converge in the direction of the bottom portion. The top portion includes plier-gripping ears 13 and 15 that facilitate the placement and removal of the segment. One or both of the ears may include an aperture 17 for the optional application of a removal string.

Figure 2:
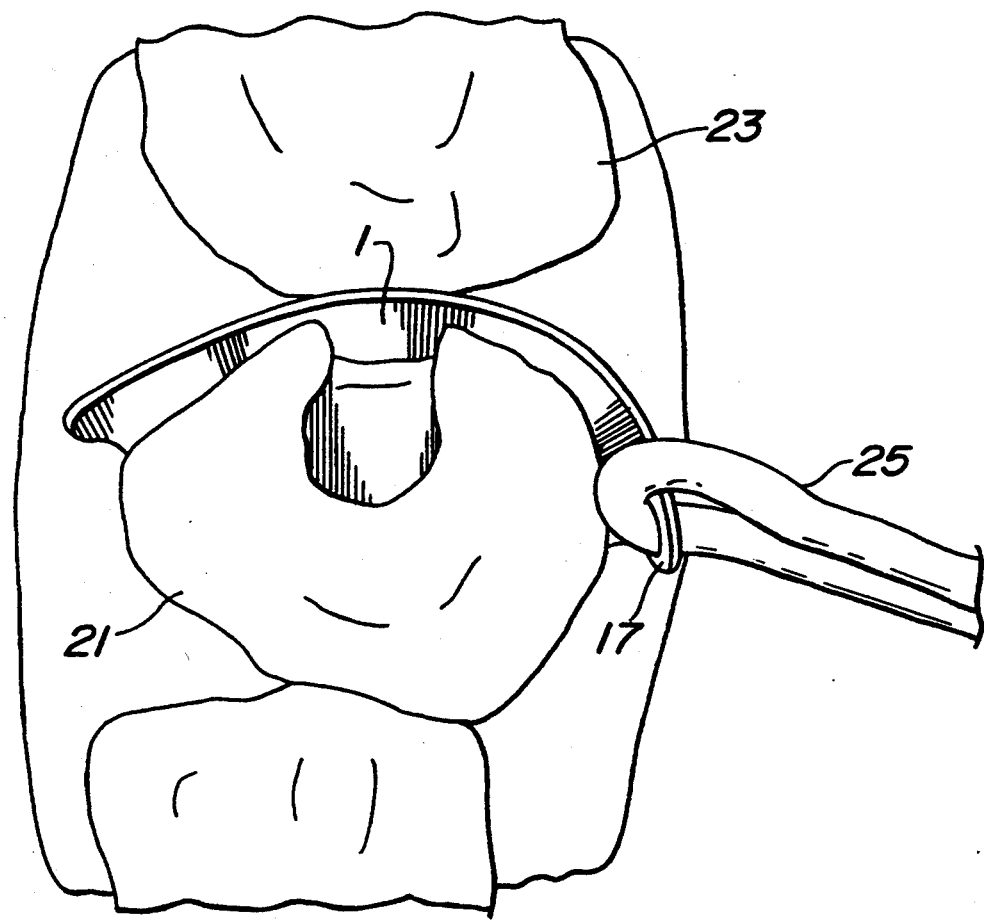
FIG. 2 shows a top isometric view of the matrix band segment of FIG. 1 interproximally positioned with the removal string applied.

The procedure of the present invention may be further described with reference to FIG. 2. The segment as shown in FIG. 1 is first contoured with contouring pliers well-known in the dental arts to replicate the original proximal anatomical form. As shown in FIG. 2, the decayed tooth structure has been removed from tooth 21 and the contoured segment applied between teeth 21 and 23. The segment is then secured against tooth 23 by the use of interproximal wooden wedges well-known in the arts (not shown in this FIGURE because as such they do not form a part of the present invention). The matrix segment is now in place for the application and condensation of restorative material. After the initial setting of the restorative material, the wooden wedge or wedges are removed. The matrix segment is then removed directly, lingually or buccally, but in the case of a silver amalgam restoration, preferably without displacement in the occlusal direction, because direct lateral withdrawal of this strip prevents forces which tend to fracture the restoration and such fractures may not be recognized immediately. With light-hardened adhesive material, strip withdrawal can be safely achieved in any direction. To assist in removing the strip, string 25 may be applied through an aperture 17 in one ear of the segment, and the strip laterally removed by pulling the string. The string also serves as a safety tether, preventing the segment from inadvertently falling into the patient's throat during placement or removal. Following strip removal, the restoration is carved in the normal manner, thus completing the restoration procedure.

The matrix band segment and procedure of the present invention has several advantages. Such a matrix can be used with a mesio-occlusal restoration, even if the treated tooth is clamped to retain a rubber dam. Full circumference matrix bands are not easily placed or stabilized on a tooth which has a rubber dam clamp in place. Another advantage is the minimal amount of time required for contouring, placing and wedging a matrix band segment. Matrix removal is also simplified. With adjacent Class II restorations for primary molars, or with three-surface Class II restorations, multiple band segments can be used with ease.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. A pre-cut matrix segment for dental restoration, comprising:
    a planar segment of sheet metal having top and bottom portions, and right and left sides;
    said top portion being wider than said bottom portion, and said sides having smooth tapered edges converging in the direction of the bottom portion;
    said top portion including two laterally-projecting ears, one on each side;
    at least one of said ears including an aperture therein; and
    a string-like implement inserted through said aperture to assist removal of said matrix segment after it has been applied between adjacent teeth.

2. The pre-cut matrix segment of claim 1, which is composed of stainless steel.

3. The pre-cut matrix segment of claim 2, wherein said matrix segment is approximately 0.0015-inches thick.

4. The pre-cut matrix segment of claim 3, which is composed of a ¼-hardness stainless steel.

5. The method of performing a dental restoration, comprising the steps of:
    applying a pre-cut matrix segment between adjacent teeth, said segment including a laterally-projecting ear at the top of one side, said ear having an aperture therethrough;
    wedging said matrix segment firmly against one of said adjacent teeth to be restored;
    applying restoration material to said one of said teeth;
    inserting a string through said aperture in said ear of said matrix segment; and
    pulling said string to remove said matrix segment from between said teeth.

* * * * *